United States Patent [19]

Chan

[11] Patent Number: 4,678,662

[45] Date of Patent: Jul. 7, 1987

[54] PYROPHOSPHATE COATING PROCESS FOR CALCIUM CARBONATE DENTAL ABRASIVES

[75] Inventor: Albert S. C. Chan, St. Louis, Mo.

[73] Assignee: Monsanto Company, St. Louis, Mo.

[21] Appl. No.: 785,702

[22] Filed: Oct. 9, 1985

[51] Int. Cl.⁴ .................. C01F 11/18; C08K 9/02; C09C 1/02; A61K 7/16

[52] U.S. Cl. ........................... 424/57; 106/306; 106/308 B; 424/49; 424/52; 424/156

[58] Field of Search .............. 106/306, 308 B; 424/49, 424/52, 57, 156

[56] References Cited

U.S. PATENT DOCUMENTS

| | | | |
|---|---|---|---|
| 2,041,473 | 5/1936 | Janota | 424/57 |
| 2,191,199 | 2/1940 | Hall | 424/57 |
| 2,272,617 | 2/1942 | Cox et al. | 424/57 |
| 2,876,168 | 3/1959 | Broge et al. | 424/57 |
| 3,137,632 | 6/1964 | Schiraldi | 424/57 |
| 3,310,372 | 3/1967 | Wright et al. | 424/57 |
| 3,597,251 | 8/1971 | Kaufman | 106/308 B |
| 3,661,610 | 5/1972 | Ferris | 106/308 B |
| 3,846,147 | 11/1974 | Tapper | 106/308 B |
| 4,122,164 | 10/1978 | Mitchell et al. | 424/52 |
| 4,301,143 | 11/1981 | Barberio | 424/57 |

FOREIGN PATENT DOCUMENTS 57-30812 7/1982 Japan.
57-30813 7/1982 Japan.

*Primary Examiner*—Ronald W. Griffin
*Attorney, Agent, or Firm*—R. Loyer

[57] ABSTRACT

Calcium carbonate particles are coated with a pyrophosphate derivative. The invention includes the coated particles, method of preparation and use in oral hygiene products.

20 Claims, No Drawings

PYROPHOSPHATE COATING PROCESS FOR CALCIUM CARBONATE DENTAL ABRASIVES

This invention relates to calcium carbonate dental abrasives having exceptional flavor and fluoride compatibility. More particularly, it relates to a process for preparing a calcium carbonate abrasive coated with a pyrophosphate.

BACKGROUND OF THE INVENTION

Calcium carbonate is well known as a dental abrasive and has long been employed as a primary abrasive in dentifrice compositions such as tooth powders and tooth pastes. It is also well known that fluoride compounds are used commonly to inhibit or reduce dental caries. Fluoride is believed to reduce the solubility of tooth enamel through the interaction of hydroxyapatite, the mineral which constitutes the major part of the dental enamel, with the fluoride so as to produce fluoroapatite which has a lower solubility in the acidic medium.

One of the disadvantages in the use of calcium carbonate dental abrasives is the "chalky" taste characteristic thereof. A second disadvantage in the use of calcium carbonate is that fluoride ion stability in its presence is usually low.

Japanese Patent No. Sho 30812 teaches a coating of calcium pyrophosphate on $CaCO_3$ using pyrophosphoric acid. While this product eliminates the chalky taste, the fluoride stability of the product is poor.

Japanese Patent No. Sho 30813 describes a process for preparing pyrophosphate-coated $CaCO_3$ using a salt such as $CaCl_2$. As would be expected, the presence of a chloride in the process is deleterious to processing equipment. Fluoride stability, while better than that demonstrated in Japanese No. 30812 is less than optimum.

If a way could be found to substantially reduce or eliminate the "chalky" taste of calcium carbonate without adversely affecting fluoride stability, and without using a corrosive salt, as in Japanese No. Sho 30813, such a method would constitute a significant advance in the art and is an object of this invention.

SUMMARY OF THE INVENTION

This invention is a pyrophosphate-coated calcium carbonate dental abrasive having improved taste and enhanced fluoride ion stability. It is produced by contacting calcium carbonate having an average particle size of 0.2–30 microns in a liquid dispersion with a pyrophosphate salt under reactive conditions fostering the limited production of one or more calcium pyrophosphate derivatives so as to provide on the surface of the calcium carbonate particles about 1–50% by weight of the calcium pyrophosphate derivatives. Oral hygiene products containing this abrasive are also included within the scope of this invention.

DETAILED DESCRIPTION OF THE INVENTION

In accordance with the invention, calcium carbonate dental abrasives are coated with a substantially insoluble and inert calcium and/or calcium alkali metal pyrophosphate.

Suitable calcium carbonate abrasives can be of the natural forms known as Aragonite and Calcite or mixtures thereof. Synthetically precipitated forms of calcium carbonates or chalk are preferred. Other forms of calcium carbonate include milled marble, powdered limestone or mined powdered products. The calcium carbonate particles have an average particle size of 0.2–30 microns with a preferred range of 2–20 microns.

Various pyrophosphate sources can be employed to provide the pyrophosphate coating on the calcium carbonate abrasive. It is important that the pyrophosphate chemisorb on the calcium carbonate abrasive through the formation of a calcium or calcium alkali metal pyrophosphate derivative by interaction with the calcium ion of the calcium carbonate abrasive. In this manner a calcium carbonate dental abrasive coated with effective amounts of substantially insoluble and inert calcium and/or calcium alkali metal pyrophosphate derivative is provided.

The amount of the calcium and/or calcium alkali metal pyrophosphate derivative chemisorbed by the calcium carbonate abrasive can vary widely with good results. Based on the total weight of the abrasive particle the amount of the calcium pyrophosphate derivative can range from less than about 1% by weight to greater than 50% by weight. Particularly advantageous results can be obtained with about 2% to 30% by weight of the calcium and/or calcium alkali metal pyrophosphate derivative. Preferably the amount of the calcium pyrophosphate derivative on the calcium carbonate abrasive is in the range of 5% to 25% by weight.

Suitable pyrophosphate sources are those which in an aqueous medium provide a reactive pyrophosphate derivative which chemisorbs on dispersed calcium carbonate abrasive through the calcium ion. Suitable pyrophosphate sources are alkali metal pyrophosphates such as sodium, potassium and lithium pyrophosphate, for example sodium trihydrogen pyrophosphate $NaH_3P_2O_7$; disodium dihydrogen pyrophosphate $Na_2H_2P_2O_7$; trisodium hydrogen pyrophosphate $Na_3HP_2O_7$; tetrasodium pyrophosphate, the potassium or lithium counterparts or mixed alkali metal counterparts thereof, such as, disodium dipotassium pyrophosphate and the like in their unhydrated as well as hydrated forms. The sodium and potassium pyrophosphates are preferred pyrophosphate sources.

The calcium carbonate dental abrasive can be coated with a calcium alkali metal pyrophosphate derivative by forming an aqueous solution of the pyrophosphate source and mixing said solution with an aqueous dispersion of the calcium carbonate abrasive for a period of time to chemisorb pyrophosphate on the calcium carbonate. To facilitate the coating of the pyrophosphate derivative on the calcium carbonate abrasive elevated temperatures can be employed for example, 100° C. with tetrasodium pyrophosphate as the pyrophosphate source. Preferably the reaction is conducted not in the presence of a significant amount of any corrosive salt such a $CaCl_2$ or NaCl.

The calcium carbonate abrasive treated in accordance with the invention demonstrates greatly improved flavor and fluoride compatibility while retaining its desirable abrasive or cleansing properties when incorporated into oral hygiene products such as toothpaste and tooth powders.

The treated calcium carbonate abrasive of this invention can be used as the sole abrasive in the oral hygiene product or can be used in conjunction with other dental abrasives. Other suitable abrasives include water-insoluble sodium or potassium metaphosphates, hydrated or anhydrous dicalcium phosphate, calcium pyrophosphate, various forms of silica, zirconium silicate and the like. Such other abrasives may be resin coated as taught in U.S. Pat. No. 3,151,027 issued Sept. 29, 1964 to W. E. Cooley et al and U.S. Pat. No. 4,157,387 issued June 5, 1979 to J. J. Benedict, incorporated herein by reference.

The total amount of abrasives employed in oral hygiene products can range from less than 5% to more than 95% by weight of the dentifrice. Generally, toothpastes contain from 20% to 60% by weight of abrasive. Abrasive average particle size preferably ranges from about 2 microns to 20 microns.

In addition to the abrasive, toothpaste compositions conventionally contain a fluoride compound, sudsing agents, binders, humectants, flavoring agents, sweetening agents and water.

Suitable fluoride compounds can be any of the compounds previously mentioned conventionally employed to provide available fluoride ion in the oral cavity. Sodium monofluorophosphate, sodium fluoride and the like, have been employed with good results in toothpastes to promote dental hygiene. Good results can be achieved employing an amount of fluoride compound to provide available fluoride ion in the range of 300 to 2000 ppm in the tooth paste, preferably 1000 ppm.

Suitable sudsing agents are generally anionic organic synthetic detergents active throughout a wide pH range. Representative of such sudsing agents used in the range of about 0.5% to 5% by weight of the composition are water-soluble salts of $C_{10}$–$C_{18}$ alkyl sulfates, such as sodium lauryl sulfate; of sulfonated monoglycerides of fatty acids, such as sodium monoglyceride sulfonates; of fatty acid amides of taurine, such as sodium N-methyl-N-palmitoyltauride; and of fatty acid esters of isethionic acid, and aliphatic acylamides, such as sodium N-lauroyl scarcosinate.

Suitable binders or thickening agents to provide the desired consistency are, for example, hydroxyethylcellulose, sodium carboxymethylcellulose, natural gums, such as gum karaya, gum arabic, gum tragacanth, colloidal silicates and finely divided silica. Generally, from 0.5% to 5% by weight of the composition can be used.

Various humectants can be used, such as glycerine, sorbitol and other polyhydric alcohols.

Suitable flavoring agents include oil of wintergreen, oil of spearmint, oil of peppermint, oil of clove, oil of sassafras and the like. Saccharin, aspartame, dextrose, levulose can be used as sweetening agents.

In the following Examples the abrasivity of the dental abrasive was determined employing the Radioactive Dentin Abrasion test which follows the procedure recommended by the American Dental Association (*Journal of Dental Research*, 55 (4) 563, 1976.) The reported Radioactive Dentin Abrasivity Index (RDA) is on the basis of calcium pyrophosphate reference standard taken as 100. All particle sizes were determined by the Coulter Counter method (ASTM C-690-80).

This invention is further illustrated by, but not limited to, the following examples wherein all parts and percentages are by weight, unless otherwise indicated.

COMPARATIVE EXAMPLE 1

To demonstrate the flavor and fluoride compatibility of the dental abrasives a conventional toothpaste base gel stock was used containing the following ingredients in percent by weight.

| Ingredient | % by Weight |
| --- | --- |
| Glycerin | 48.00 |
| Sodium carboxymethylcellulose | 2.00 |
| Methyl P—hydroxy benzoate | 0.10 |
| Propyl P—hydroxy benzoate | 0.02 |
| Saccharin | 0.44 |
| Water | 49.44 |

The dental abrasive was added to the base gel stock in the ratio of 80 parts by weight abrasive to 107.3 parts by weight of base stock with stirring. To the resulting mixture 7.72 parts by weight of a 20% aqueous solution of sodium monofluorophosphates (MFP), 2.98 parts by weight of sodium lauryl sulfate and 2 parts by weight of flavoring agent blend were added and thoroughly mixed with a mechanical agitator to provide 200 parts by weight commercial type of a commercial type formulated toothpast containing 1000 ppm of available fluoride. The paste was evaluated for flavor compatibility, chalky taste, and fluoride compatibility using accelerated aging test to simulate long term shelf stability by placing the toothpaste in one-ounce standard aluminum tubes and aging in an oven at 60° C. for five days and measuring the soluble fluoride concentration potentiometrically.

Using the above procedure and techniques, a calcium carbonate dental abrasive, having an average particle size of 27 microns and an RDA value of 192, demonstrated a distinctly unpleasant chalky taste and a retention of 946 ppm of available fluoride in the accelerated test.

EXAMPLE 2

This Example employs tetrasodium pyrophosphate as the pyrophosphate source.

Tetrasodium pyrophosphate, 446 grams (1 mole) was stirred in two liters of water and 360 grams of 37% hydrochloric acid (3.65 moles) was added with stirring to form a clear solution. The solution was then added to rapidly stirred mixture of 860 grams of the calcium carbonate abrasive, as used in Example 1, in three liters of water. Stirring was continued overnight and then the solid product was filtered, rinsed with about four liters of water and the filtered wet cake was air-dried and pulverized. Analysis of the dried product showed pyrophosphate-coated the calcium carbonate contained 14% by weight of $P_2O_5$, having an average particle size of 11.5 microns and a RDA of approximately 151.

Using the procedures and techniques of Example 1, the coated calcium carbonate abrasive was mixed with the base gel stock and the MFP, sodium lauryl sulfate and the flavoring agent blend were added with thorough mixing to provide a formulated toothpaste. The toothpaste had no chalky taste and retained 1000 ppm of available fluoride in the accelerated aging test.

EXAMPLE 3

This example employs disodium dihydrogen pyrophosphate as the pyrophosphate source.

With stirring, 209 grams of disodium dihydrogen pyrophosphate (SAPP) was dissolved in 1500 ml of water at ambient temperature. The SAPP solution was added to a stirred slurry containing 500 grams of the calcium carbonate abrasive of Example 1 and 1000 ml of water. Stirring was continued for about 3 hours and the solid product was filtered, rinsed with water and the filter wet cake was air-dried. Analysis of the dried product showed the pyrophosphate-coated calcium carbonate contained about 18% by weight of $P_2O_5$, having an RDA value of about 162.

Following the procedure and techniques of Example 1, this coated calcium carbonate abrasive was formulated into a toothpaste. The resultant toothpaste showed excellent flavor compatibility, no chalky taste, and retained 956 ppm of available fluoride in the accelerated aging test.

EXAMPLE 4

At reflux temperature, about 100° C., 157 grams of tetrasodium pyrophosphate decahydrate and 500 grams of the calcium carbonate abrasive of Example 1 were stirred for 3 hours. The slurry was filtered and the solid product was rinsed with one liter of water, filtered and air dried and pulverized. Analysis of the dried product showed the pyrophosphate-coated calcium carbonate abrasive contained about 7.3% by weight $P_2O_5$.

Following the procedure and techniques of Example 1, this coated calcium carbonate abrasive was formulated into a toothpaste. The resultant toothpaste showed excellent flavor compatibility, no chalky taste, and retained 1000 ppm of available fluoride in the accelerated aging test.

EXAMPLE 5

The general procedures and techniques of Example 4 were repeated except spray dried calcium carbonate (M-48 from Mississippi Lime Co.) having an average particle size of 13.7 microns and a RDA value of 72 was used and was refluxed with the tetrasodium pyrophosphate for four hours. The resultant coated calcium carbonate abrasive had an average particle size of 10 microns and a RDA value of 76. When formulated into a toothpaste it showed excellent flavor compatibility, no chalky taste, and retained 788 ppm of available fluoride in the accelerated aging test. An untreated sample of the same calcium carbonate imparted a chalky taste and retained 623 ppm of available fluoride in the same aging test.

EXAMPLE 6

Following the general procedures and techniques of Examples 2, 3 and 4 but replacing the MFP with sodium fluoride to provide a toothpaste containing 1000 ppm of available fluoride produced a toothpaste having excellent flavor compatibility and improved available fluoride retention when compared to toothpaste prepared with uncoated calcium carbonate.

Although the invention has been described in terms of specified embodiments which are set forth in considerable detail, it should be understood that this is by way of illustration only and that the invention is not necessarily limited thereto since alternative embodiments in operating techniques will become apparent to those skilled in the art in view of the present disclosure. Accordingly, modifications are contemplated which can be made without departing from the spirit of the described invention.

What is claimed is:

1. A treated calcium carbonate abrasive being the product of the method comprising contacting pulverized calcium carbonate having an average particle size of 0.2-30 microns in a liquid dispersion with an alkali metal pyrophosphate source under reactive conditions fostering the limited production of a pyrophosphate derivative selected from the group consisting of calcium pyrophosphate, calcium alkali metal pyrophosphate, and mixtures thereof so as to provide a coated calcium carbonate particle wherein the coating comprises from about 1-50% by weight of the particle of the pyrosphosphate derivative.

2. The abrasive of claim 1 wherein the amount of pyrophosphate derivative is from about 2% to 30% by weight based on the total weight of the abrasive.

3. The abrasive of claim 1 wherein the amount of pyrophosphate derivative is 5-25% by weight.

4. The abrasive of claim 1 having an average particle size in the range from about 2 microns to 20 microns.

5. The abrasive of claim 1 wherein the pyrophosphate source is an alkali metal pyrophosphate.

6. The abrasive of claim 5 wherein the pyrophosphate source is selected from the group consisting of sodium and potassium pyrophosphates.

7. The abrasive of claim 1 wherein the pyrophosphate source is a mixed alkali metal pyrophosphate.

8. The abrasive of claim 1 wherein the pyrophosphate derivative is hydrated calcium pyrophosphate.

9. The abrasive of claim 1 wherein the pyrophosphate derivative is calcium alkali metal pyrophosphate.

10. A method for preparing a coated pyrophosphate abrasive comprising contacting essentially unhalogenated pulverized calcium carbonate having an average particle size of about 0.2-20 microns in a liquid dispersion with an alkali metal pyrophosphate derivative source under reactive conditions fostering the limited production of a calcium alkali metal pyrophosphate derivative on the surface of the calcium carbonate particles in the amount of about 1-50% by weight of the particle.

11. The method of claim 10 wherein the amount of the pyrophosphate derivative on the calcium carbonate is in the range of about 2% to 30% by weight.

12. The method of claim 11 wherein the amount of the pyrophosphate derivative on the calcium carbonate is in the range of about 5% to 25% by weight.

13. The method of claim 12 wherein the pyrophosphate source is disodium dihydrogen pyrophosphate.

14. The method of claim 12 wherein the pyrophosphate source is tetrasodium pyrophosphate.

15. The method of claim 14 wherein reactive conditions include elevated temperature.

16. An oral hygiene product comprising from about 5% to about 95% by weight of a calcium carbonate abrasive having thereon a coating of a calcium alkali metal pyrophosphate derivative.

17. The oral hygiene product of claim 16 further comprising a fluoride compound in an amount to provide from 300 to 2000 ppm of available fluoride.

18. The oral hygiene product of claim 17 wherein the amount of the calcium pyrophosphate derivative on the calcium carbonate is from about 5% to 25% by weight.

19. The oral hygiene product of claim 18 wherein the pyrophosphate derivative is selected from the group consisting of $CaNa_2 P_2O_7.4H_2O$ and mixtures thereof.

20. The oral hygiene product of claim 18 wherein the pyrophosphate derivative is selected from the group consisting of calcium pyrophosphate and mixtures thereof.

* * * * *